United States Patent
Michalske et al.

(10) Patent No.: US 7,584,642 B2
(45) Date of Patent: Sep. 8, 2009

(54) PROCEDURE TO CALIBRATE A SIGNAL SUPPLIED BY A LAMBDA SENSOR AND DEVICE TO IMPLEMENT THE PROCEDURE

(75) Inventors: Andreas Michalske, Leonberg (DE); Thomas Steinert, Weinstadt (DE)

(73) Assignee: Robert Bosch GmbH (DE)

( * ) Notice: Subject to any disclaimer, the term of this patent is extended or adjusted under 35 U.S.C. 154(b) by 466 days.

(21) Appl. No.: 11/602,692

(22) Filed: Nov. 20, 2006

(65) Prior Publication Data

US 2007/0113615 A1    May 24, 2007

(30) Foreign Application Priority Data

Nov. 23, 2005 (DE) ........................ 10 2005 056 152

(51) Int. Cl.
*G01N 3/21* (2006.01)
(52) U.S. Cl. ........................................................ 73/1.06
(58) Field of Classification Search ........................ None
See application file for complete search history.

(56) References Cited

FOREIGN PATENT DOCUMENTS

| DE | 38 27 978 A1 | 5/1989 |
|----|---|---|
| DE | 198 10 483 A1 | 9/1999 |
| DE | 199 19 427 A1 | 11/2000 |
| DE | 100 36 129 A1 | 2/2002 |

OTHER PUBLICATIONS

Dr. rer. nat. H. Schwars, Dr. rer. nat. B. Blaich, "Ottomotor-Management", Publisher Vieweg, 1st Edition, 1998, ISBN 3-528-03877-2, pp. 22-23.

*Primary Examiner*—Robert R Raevis
(74) *Attorney, Agent, or Firm*—Merchant & Gould P.C.

(57) ABSTRACT

A procedure for the calibration of the lambda measuring signal supplied by the wideband lambda sensor, which is disposed in the exhaust gas area of an internal combustion engine, and a device to implement the procedure are proposed. During the procedure, a correction value is used to ascertain a unit of measurement for the lambda actual value, whereby the correction value is ascertained during a specified operating state of the internal combustion engine, in which no fuel metering occurs and the engine rotational speed of the internal combustion engine lies above a threshold value. The correction value—is ascertained as a function of the sensor temperature of the wideband lambda sensor during a specified operating state.

10 Claims, 1 Drawing Sheet

Figure 1:
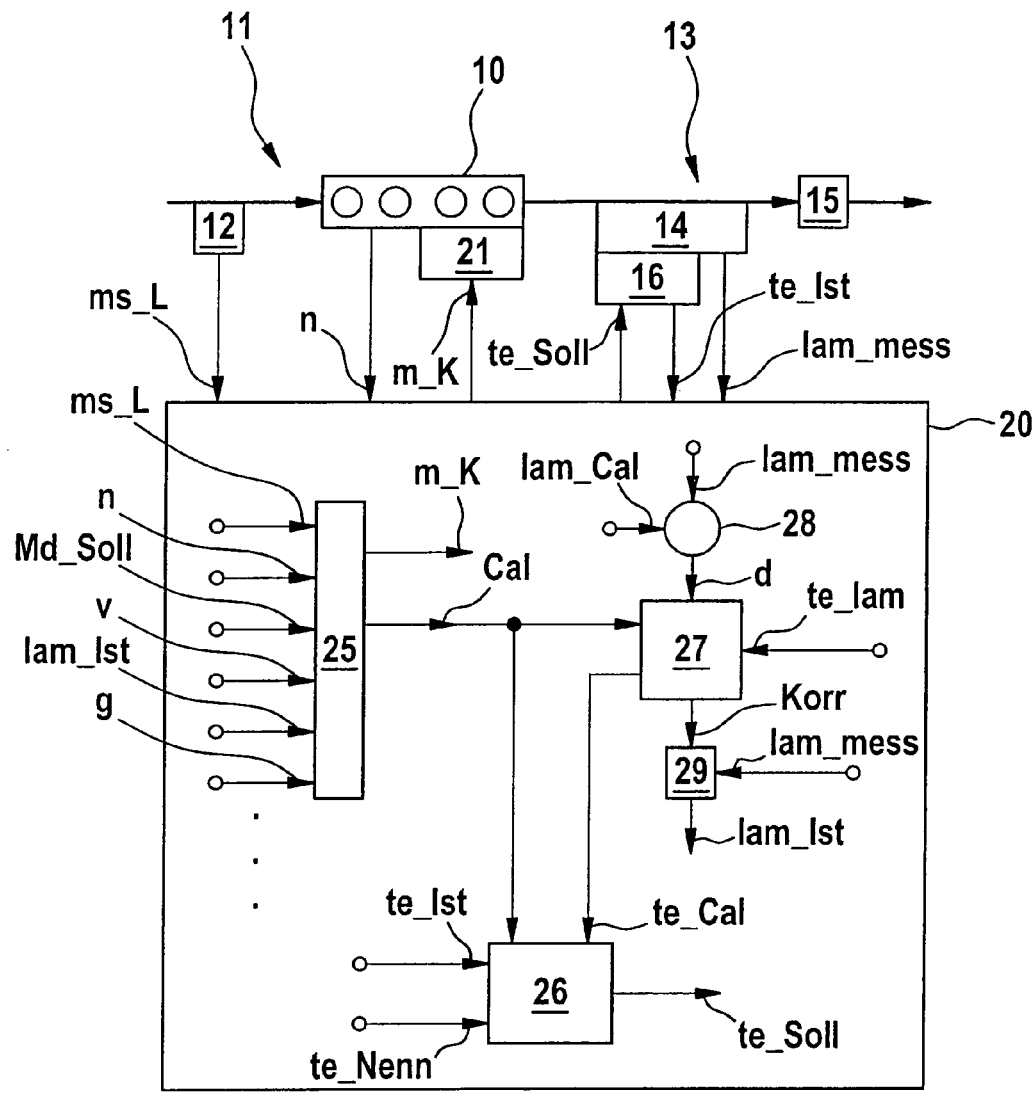

PROCEDURE TO CALIBRATE A SIGNAL SUPPLIED BY A LAMBDA SENSOR AND DEVICE TO IMPLEMENT THE PROCEDURE

The invention proceeds from a procedure to calibrate the signal supplied by a wideband lambda sensor and a device to implement the procedure according to the class of the independent claims.

In the German patent DE 198 10 483 A1 a procedure is described to determine the sensor signal offset of HC— and/or $NO_x$ sensors. In an operating state of an internal combustion engine and a catalytic converter, in which no HC—, respectively $NO_x$ occur, the signal supplied by the sensor is evaluated as an offset-signal and used to calibrate the sensor signal. A condition, in which no HC—, respectively $NO_x$-emissions occur, is, for example, present during an overrun fuel cut-off of the internal combustion engine, which is intended for fuel saving, if specified operating conditions exist.

In the German patent DE 38 27 978 A1, a procedure and a device are described for a constant lambda regulation, in both of which the signal supplied by a voltage jump lambda sensor is processed in such a manner, that a constant lambda regulation is possible in the range around lambda=1. The procedure is based upon the fact that it does not work with sensor voltage norm deviations, but that it determines lambda value norm deviations according to a sensor characteristic connection between sensor voltage values and lambda values. The signal supplied by the voltage jump lambda sensor depends upon the sensor temperature. Provision is, therefore, made for a correction of the lambda signal supplied by the jump lambda sensor as a function of the sensor temperature to calibrate the sensor signal. Provision is made for an additional correction for a still more accurate calibration by ascertaining the sensor signal offset during the overrun fuel cut-off of the internal combustion engine.

In the German patent DE 100 36 129 A1 a procedure is described to measure an exhaust gas composition with a jump lambda sensor, which has a sensor heater. Provision is made for a correction of the sensor signal as a function of the sensor temperature, at which every signal voltage is assigned a correction voltage as a function of the sensor temperature.

In the German patent DE 199 19 427 A1, a procedure is described to correct the signal supplied by a wideband lambda sensor, in which the slope of the characteristic curve of the sensor signal is corrected as a function of the sensor signal, which occurs during an overrun fuel cut-off of the internal combustion engine.

In the trade manual "Ottomotor-Management/Bosch", Publisher Vieweg, 1. Edition, 1998, pages 22-23, a wideband lambda sensor is described, which has a sensor chamber that is connected by way of a diffusion barrier with a gas chamber. An inner pumping electrode is disposed in the sensor chamber, which forms a pumping cell with an outer pumping electrode and an electrolyte, which guides the oxygen ions, lying between the pumping electrodes. With the pumping cell, oxygen ions can be pumped by way of the electrolyte out of the sensor chamber or into the sensor chamber.

A measuring cell is present next to the pumping cell, which lies between the inner pumping electrode and a reference gas electrode, whereby an electrolyte, which guides oxygen ions, is likewise disposed between the inner pumping electrode and the reference gas electrode. The measuring cell corresponds to a Nernst cell, at which the potential difference formed in thermodynamic balance between the inner pumping electrode and the reference electrode is proportional to the logarithm of the ratio of the partial pressure of the gas being tested in the sensor chamber and the partial pressure of the gas being tested in the air reference. The goal of a measurement of the exhaust gas lambda is to influence the oxygen partial pressure in the sensor chamber in such a manner, that the Nernst potential stays constantly at a specified value, which preferably corresponds to Lambda=1. For this purpose, a circuit arrangement changes an electrical pumping current, with which the outer pumping electrode is charged. The polarity and the amount of pumping current are dependent upon whether and in what amount the specified Nernst potential is fallen short of or exceeded. The pumping current which arises is a unit of measurement for the exhaust gas lambda.

The task underlying the invention is to indicate a procedure to calibrate the signal supplied by a wideband lambda sensor and a device to implement the procedure.

The task is solved in each case by the characteristics indicated in the independent claims.

Provision is made to ascertain a correction value to provide at least a unit of measurement for the lambda actual value in the procedure according to the invention for the calibration of the signal supplied by the wideband lambda sensor, which is disposed in the exhaust gas area of an internal combustion engine. The ascertainment of the correction value is conducted during a specified operating state of the internal combustion engine, in which no metering of the fuel occurs and the engine rotational speed lies above a threshold value. Provision is made according to the invention to ascertain the correction value as a function of the temperature of the wideband lambda sensor during the specified operating state of the internal combustion engine.

Based upon experiments it was determined that not only the lambda signal supplied by a generally unheated jump lambda sensor but also the signal supplied by a wideband lambda sensor can depend upon the sensor temperature, although the operating temperature of a wideband lambda sensor is maintained at a specified rated temperature by a sensor heater.

The procedural approach according to the invention takes into account, should the occasion arise, a standard deviation of the wideband lambda sensors, which is present due to temperature and manufacture. It does this through the calibration of the signal supplied by the wideband lambda sensor during operation when the wideband lambda sensor is in an installed state. Furthermore, should a temperature dependent drift due to deterioration arise, it can especially be taken into account during the operating time.

Provision is made preferably for the calibration of the signal supplied by the wideband lambda sensor not only at concrete sensor temperatures but for temperature ranges.

Advantageous embodiments and configurations of the procedural approach according to the invention result from the dependent claims.

Provision is made in one embodiment for at least one unit of measurement for the actual temperature measured to be used as the sensor temperature. The actual temperature is available, when provision is made for a closed loop temperature control. Alternatively at least one unit of measurement for the specified set point temperature or an estimated temperature value can be used as the sensor temperature. The set point temperature is in any case available in the control unit regardless if provision is made for an open-loop or closed-loop controlled heating of the sensor.

Provision is made in an embodiment for different calibration temperatures to be selectively specified as the set point temperature. The selective specification of set point temperatures is especially advantageous for those, for which no correction value has been ascertained up till now.

Provision is made in one embodiment for the beginning and/or the end of the specified operating state of the internal combustion engine, in which no fuel metering occurs and the engine rotational speed lies above a specified threshold value, to be established as a function of the load signal of the internal combustion engine. Furthermore, at least the gear of the transmission, which is engaged, and/or the driving speed of the motor vehicle is taken into account, in which the internal combustion engine is deployed as a power drive.

The device according to the invention to calibrate the signal supplied by a wideband lambda sensor concerns initially a control unit, which is specially manufactured to implement the procedure.

The control unit contains particularly preferably an operating state ascertainment for the specified operating state, in which no fuel metering occurs and the engine rotational speed lies above the threshold value, as well as a correction value ascertainment. Furthermore, provision is made preferably for a set point temperature establishment for the set point temperature of the wideband lambda sensor in the control unit.

The control unit contains preferably at least one electrical storage, in which the procedural steps are deposited as a computer program.

Additional advantageous embodiments and configurations of the procedural approach according to the invention result from additional claims and from the following description.

Figure 2:
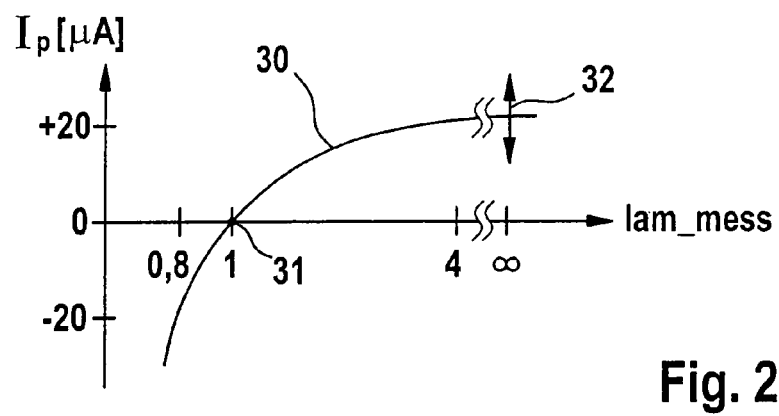

FIG. 1 shows a technical layout, in which a procedure according to the invention is operating and FIG. 2 shows a characteristic curve of a wideband lambda sensor.

FIG. 1 shows an internal combustion engine 10, in whose air intake area 11 an air sensor 12 and in whose exhaust gas area 13 a wideband lambda sensor as well as an exhaust gas treatment device are disposed.

The air sensor 12 provides an air signal ms_L to the control unit 20; the internal combustion engine 10 provides an engine rotational speed n; a sensor heater 16 attached to the wideband lambda sensor 14 provides an actual temperature te_Ist of the wideband lambda sensor 14 and the wideband lambda sensor 14 provides a lambda measuring signal lam_mess.

The control unit 20 provides a fuel signal m_K to a fuel metering 21 attached to the internal combustion engine 10 and a set point temperature te_Soll to the sensor heater.

The control unit 20 contains an operating state ascertainment 25, which provides the air signal ms_L, the engine rotational speed n, a load signal Md_Soll, a driving speed v, a lambda actual value lam_Ist, a gear update g, as well as additional unspecified signals.

The operating state ascertainment 25 provides a signal Cal, which characterizes a specified operating state of the internal combustion engine 10. The operating state ascertainment additionally supplies the fuel signal m_K.

The signal Cal, which characterizes the specified operating state of the internal combustion engine 10 is supplied to a set point temperature establishment 26, which supplies the set point temperature te_Soll for the heater of the wideband lambda sensor 14. The actual temperature te_Ist as well as a specified rated temperature te_Nenn of the wideband lambda sensor 14 are supplied to the set point temperature establishment 26. Furthermore, the set point temperature establishment 26 is supplied with a calibration temperature te_Cal provided by the correction value ascertainment 27.

The lambda measuring signal lam_mess is compared with a lambda calibration signal lam_Cal in a comparator 28. The difference d ascertained by the comparator 28 is provided to the correction value ascertainment 27, which additionally is supplied with the signal Cal, which characterizes the specified operating state of the internal combustion engine 10, as well as with a sensor temperature te_lam. Beside the calibration temperature te_Cal the correction value ascertainment 27 supplies a correction value Korr, with which the lambda measuring signal lam_mess is corrected to the lambda actual value lam_Ist in a lambda actual value ascertainment 29.

FIG. 2 shows a characteristic curve 30 of the wideband lambda sensor 14, which assigns the lambda measuring value lam_mess to a pumping current Ip. The characteristic curve depicted in FIG. 2 corresponds basically to the characteristic curve of the wideband lambda sensor 14 mentioned previously in the application under State of the Art.

A pumping current Ip of zero corresponds to a lambda measuring value lam_mess=1. A fulcrum point 31 of the characteristic curve 30 is located at lambda=1. A negative pumping current Ip is supposed to emerge in the case of an oxygen debt and a positive pumping current in the case of an oxygen surplus.

Beside the lambda measuring value lam_mess, the lambda measuring values lam_mess of 0.8 and 4 are plotted, whereby a pumping current of, for example, minus 20 microamperes corresponds to a lambda measuring value lam_mess of 0.8, and a pumping current of, for example, plus 20 microamperes corresponds to a lambda measuring value lam_mess of 4. The characteristic curve extends in theory up to lambda=infinity, whereby the pumping current Ip no longer significantly rises in regard to the current at, for example, lambda=4. A measuring point displacement 32 is plotted at lambda=infinity.

The procedure according to the invention works in the following manner: The operating state ascertainment 25 ascertains the fuel signal m_K, which is supplied to the fuel metering 21, for example, as a function of the engine rotational speed n and/or the load signal Md_Soll and/or the air signal ms_L and/or the lambda actual value lam_Ist.

The air signal ms_L is a unit of measurement for the air stream flowing into the internal combustion engine 10. The load signal Md_Soll corresponds, for example, to a torque set point, which is derived, for example, from the position of an unspecified accelerator pedal, which is disposed in a likewise unspecified motor vehicle, in which provision is made for the internal combustion engine 10 to be the power drive.

The operating state ascertainment 25 especially ascertains the signal Cal, which characterizes the specified operating state, whereby the specified operating state is ascertained at least from the engine rotational speed n and, for example, from the load signal Md_Soll. The specified operating state distinguishes itself in such a way, that the fuel signal is practically zero, so that the internal combustion engine 10 is not provided with fuel. Simultaneously it is assumed, that the engine rotational speed n of the internal combustion engine 10 lies above a threshold value. The specified operating state corresponds to a sliding operation of the internal combustion engine 10, during which at least a slight air stream occurs in the air intake area 11 and the exhaust gas area 13, which corresponds predominantly to the composition of the ambient air, while no fuel combustion is taking place in the internal combustion engine 10.

The signal Cal indicates, that the lambda measuring signal lam_mess of the wideband lambda sensor 14 should correspond to a lambda which is theoretically infinity. This lambda then corresponds to an oxygen concentration in the exhaust gas area 13 of approximately 21%, thus the oxygen concentration of the ambient air. When the signal Cal is present, a calibration of the lambda measuring signal lam_mess supplied by the wideband lambda sensor can, therefore, occur, because the oxygen concentration in the exhaust gas area is known.

At this point it should be noted, that the correction described in the example of embodiment and called for in the claims can take place on the basis of lambda values and similarly on the basis of oxygen concentrations or on the basis of other parameters, which can be derived.

The calibration of the measuring signal lam_mess supplied by the wideband lambda sensor 14 makes possible not only a compensation for the standard dispersions of the wideband lambda sensor 14, but also for the effects of deterioration, for example, drift due to deterioration during the operation of the wideband lambda sensor 14 in an installed state. Beyond this the lambda tolerances are constricted, in order to constrict the tolerances of the exhaust gas before the catalytic converter. For this purpose a return channeling of the exhaust gas can be used. Furthermore, an optimal operation of the exhaust gas treatment device 15 can be ensured over its entire life span.

The exhaust gas treatment device 15 contains, for example, at least one catalytic converter and/or a particle filter. The composition of the exhaust gas has a considerable influence over the exhaust gas purification and/or the exhaust gas conditioning by means of a catalytic converter. Provided that the exhaust gas treatment device 15 contains a particle filter, which from time to time is regenerated by a flame cleaning of the particles, the oxygen concentration in the exhaust gas area plays a significant role in determining the speed at which the particles are burned off, which additionally influences the temperature in the particle filter. Furthermore, the oxygen concentration in the exhaust gas plays a significant role during a simulation of the degree of depletion of the particle filter, for which provision is made if necessary.

The comparator 28 compares the lambda measuring signal lam_mess with the lambda calibration signal lam_Cal and provides the difference d as a function of the result. The lambda calibration signal lam_Cal would theoretically have to be established at the value infinity. The correction is worked in an expedient fashion on the basis of the reciprocals of lambda or, for example, on the basis of oxygen concentrations. As a result of this, the quotient between the lambda measuring signal lam_mess and the lambda calibration signal lam_Cal can also be ascertained in place of the difference d. In this case it is more expedient to select an evaluation on the basis of the oxygen concentration, in order to avoid dividing by infinity, respectively by zero.

The difference d is used in the correction value ascertainment 27 for the provision and deposit of the correction value Korr. The correction value Korr corrects the lambda measuring signal lam_mess to the lambda actual value lam_Ist in the lambda actual value ascertainment 29. The correction occurs, for example, by means of an intervention into the characteristic curve 30 depicted in FIG. 2. The correction makes provision for a change in the slope of the characteristic curve 30, whereby it is assumed, that the characteristic curve 30 is rotated around the fulcrum point 31. The correction of the slope occurs, for example, by multiplying the lambda measuring signal lam_mess by the correction value Korr at lambda=infinity. The multiplication of the lambda measuring signal lam_mess by the correction value corresponds to the measuring point displacement 32. Provided that a quotient is ascertained in place of the difference d, the correction value Korr is a unit of measurement for the reciprocal of the quotient.

It has been determined on the basis of experiments, that the sensor temperature te_lam of the wideband lambda sensor has an influence on the lambda measuring signal lam_mess. Provision is made, therefore, according to the invention for a more extensive correction of the lambda measuring signal lam_mess supplied by the wideband lambda sensor 14 as a function of the sensor temperature te_lam during the specified operating state of the internal combustion engine 10, in which no fuel metering occurs and the engine rotational speed lies above the threshold value.

The correction value ascertainment 27 takes, therefore, additionally into account the sensor temperature te_lam when ascertaining and depositing the correction values Korr. The sensor temperature te_lam is preferably the actual temperature te_Ist of the wideband lambda sensor 14, which is available, if the sensor heater 16 is included in a closed-loop temperature control concept. Provided the actual temperature te_Ist is not available, an estimated temperature value or the specified temperature set point te_Soll within the scope of an open-loop temperature control concept can, for example, be used as the sensor temperature te_lam.

At this point it should be noted, that the calibration is implemented not only at specified concrete temperature set points te_Soll, but especially for specified set point temperature ranges.

The calibration occurs in an expedient fashion not only at the rated temperature te_Nenn specified by the manufacturer of the wideband lambda sensor 14, respectively the rated temperature range specified, but also especially includes a temperature range lying below this; so that already during the warm-up phase and/or in the cool-down phases of the wideband lambda sensor 14, a lambda actual value lam_Ist, which is correct as possible, can be maintained.

A first possibility to selectively specify the set point temperature te_Soll is possible with the calibration temperature te_Cal, which supplies the correction value ascertainment 27 as a function based upon which correction values Korr are still missing as a function of the sensor temperature te_lam. The set point temperature establishment 26 establishes the set point temperature te_Soll as a function of the requested calibration temperature te_Cal, to which the sensor heater 16 is supposed to heat the wideband lambda sensor 14.

Another possibility to selectively specify different set point temperatures te_Soll is that the set point temperature establishment 26 at the emergence of the signal Cal puts the set point temperatures te_Soll, which are deposited, for example, in a table and at which provision is made for a calibration, into chronological order. If need be, the actual temperature te_Ist, which is made available to the set point establishment 26, can be used for the targeted selection of the set point temperatures te_Soll, whereby the set point temperature te_Soll to be specified should deviate as little as possible from the existing actual temperature te_Ist. Provision is also especially made for the calibration, which is implemented continually when the signal Cal is present, at the rated temperature te_Nenn, respectively in the rated temperature range, of the wideband lambda sensor 14, in order also to be able to compensate there for a drift due to deterioration.

The invention claimed is:

1. A method of calibrating a lambda measuring signal supplied by a wideband lambda sensor disposed in an exhaust gas area of an internal combustion engine, the method including:
   determining a correction value as a function of a sensor temperature of the wideband lambda sensor during a specified operating state of the internal combustion engine, in which no fuel metering occurs and an engine rotational speed of the internal combustion engine lies above a threshold value;
   determining a unit of measurement for a lambda actual value from the correction value.

2. A method according to claim 1, wherein the unit of measurement for a lambda actual value is used as a sensor temperature.

3. A method according to claim 1, wherein a specified set point temperature is used as a sensor temperature.

4. A method according to claim 1, wherein a rated temperature of the wideband lambda sensor is used as a set point temperature.

5. A method according to claim 1, further comprising establishing a beginning and end of the specified operating state of the internal combustion engine, as a function of a load signal of the internal combustion engine or of a gear, which is engaged in a transmission, or of a driving speed of a motor vehicle, in which the internal combustion engine is deployed as a power drive.

6. A method according to claim 1, further comprising correcting a slope of a characteristic curve by way of a rotation of the characteristic curve around a fulcrum point, which lies at a lambda value of 1.

7. A method according to claim 1, wherein a sensor temperature is set to a specified set point temperature.

8. A device for the calibration of a lambda measuring signal supplied by a wideband lambda sensor disposed in the exhaust gas area of an internal combustion engine having a control unit for determining a correction value as a function of a sensor temperature of the wideband lambda sensor during a specified operating state of the internal combustion engine, in which no fuel metering occurs and an engine rotational speed of the internal combustion engine lies above a threshold value, and for determining a unit of measurement for a lambda actual value from the correction value.

9. A device according to claim 8, wherein the control unit contains a operating state ascertainment for the specified operating state as well as a correction value ascertainment.

10. A device according to claim 8, wherein the control unit contains a set point temperature establishment for a set point temperature of the wideband lambda sensor.

* * * * *